United States Patent
Loyd, Sr. et al.

(10) Patent No.: US 6,486,452 B2
(45) Date of Patent: Nov. 26, 2002

(54) FLEXIBLE HEATER ASSEMBLY

(76) Inventors: Partick V. Loyd, Sr., 1615 Old Annapolis Rd., Woodbine, MD (US) 21797; Bruce Edward Jones, Jr., 4536 Lower Beckleysville Rd., Hampstead, MD (US) 21074

(*) Notice: Subject to any disclaimer, the term of this patent is extended or adjusted under 35 U.S.C. 154(b) by 0 days.

(21) Appl. No.: 09/835,202

(22) Filed: Apr. 13, 2001

(65) Prior Publication Data

US 2002/0047007 A1 Apr. 25, 2002

Related U.S. Application Data

(62) Division of application No. 09/695,105, filed on Oct. 24, 2000.

(51) Int. Cl.[7] .................................................. H05B 3/06
(52) U.S. Cl. ........................ 219/530; 219/528; 219/549; 219/212
(58) Field of Search ................................. 219/530, 505, 219/528, 549, 730, 212; 206/524.8; 338/22 R, 210; 383/110; 392/346; 5/644, 421; 126/263.07, 263.01

(56) References Cited

U.S. PATENT DOCUMENTS

| | | | | |
|---|---|---|---|---|
| 3,648,469 A | * | 3/1972 | Chapman ..................... | 219/528 |
| D282,515 S | * | 2/1986 | Wada et al. ................... | 5/421 |
| 4,859,250 A | * | 8/1989 | Buist .......................... | 219/212 |
| 4,868,898 A | * | 9/1989 | Seto ........................... | 219/528 |
| 5,354,131 A | * | 10/1994 | Mogil ......................... | 383/110 |
| RE34,929 E | * | 5/1995 | Kristen ..................... | 206/524.8 |
| 5,584,086 A | * | 12/1996 | Van Winkle et al. ........... | 5/644 |
| 5,805,766 A | * | 9/1998 | Wang ......................... | 219/530 |
| 5,884,006 A | * | 3/1999 | Frohlich et al. ............. | 392/346 |
| 6,031,212 A | * | 2/2000 | Westerman et al. ......... | 219/530 |
| 6,108,489 A | * | 8/2000 | Frohlich et al. ............. | 392/346 |
| 6,150,647 A | * | 11/2000 | Anderson et al. ........... | 219/730 |
| 6,215,954 B1 | * | 4/2001 | Hyatt ......................... | 392/346 |

* cited by examiner

*Primary Examiner*—Teresa Walberg
*Assistant Examiner*—Fadi H. Dahbour
(74) *Attorney, Agent, or Firm*—William S. Ramsey

(57) ABSTRACT

A flexible heater or cooler which includes a flexible, conformal, thermally conductive container filled with thermally conductive material. A thermal element within the container or in contact with the outside of the container provides heat to the container or removes heat from the container. The thermal element is powered by a low voltage direct current electrical source. A sensor for determining the temperature of the thermally conductive material is also included. The thermal element, electrical source, and sensor are in communication by connectors with a solid state continuous temperature controller. In operation, the electrical source provides power to the thermal element, thereby heating or cooling the thermally conductive material within the container. The temperature in the container is determined by the sensor and the controller controls the power delivery to the thermal element in response to the setting on the controller and the temperature in the container.

2 Claims, 4 Drawing Sheets

FLEXIBLE HEATER ASSEMBLY

CROSS-REFERENCE TO RELATED APPLICATIONS

This is a divisional application of Ser. No. 09/695,105, filed Oct. 24, 2000, pending.

STATEMENT REGARDING FEDERALLY SPONSORED RESEARCH OR DEVELOPMENT

Not Applicable.

REFERENCE TO A MICROFICHE APPENDIX

BACKGROUND OF THE INVENTION

1. Field of the Invention

This invention relates to flexible heating and cooling devices in which an electric current provides the power for heating and cooling.

2. Description of Related Art Including Information Disclosed Under 37 CFR 1.97 and 37 CFR 1.98

U.S. Pat. No. 4,388,607 discloses conductive polymer compositions made of carbon black dispersed in a crystalline copolymer. The use of such compositions in self-regulating heaters was disclosed.

U.S. Pat. No. 4,764,664 discloses a process for reducing the contact resistance between an electrode and a conductive polymer composition, thereby increasing the stability of a heating device constructed of such a polymer and electrodes. In the process, the electrode is heated to a temperature above the melting point of the composition before contacting the composition.

U.S. Pat. No. 4,777,346 discloses a liquid or gel filled pillow containing a resistance heater which is activated when a person compresses a switch formed of a layer of non-conductive foam located between two conductive layers.

U.S. Pat. No. 4,907,340 discloses a method for increasing the stability of a conductive polymer composition, which consists of cross-linking the composition using irradiation.

U.S. Pat. No. 5,111,032 discloses a self-regulating strip heater made of conductive polymer with embedded electrodes surrounded by a strengthening braid. The thermal efficiency of the heater is increased by impregnating the interstices of the braid with an outer insulating layer.

U.S. Pat. No. 5,653,741 discloses a flexible pad for heating or cooling a body part which has thermoelectric devices attached to a thermal conductive material. The thermoelectric devices heat or cool depending on the polarity of the current which power them. An enclosure surrounds the thermoelectric devices and fans are used to cool the heat sink portion of the thermoelectric devices when used to cool the body part.

The KA SMARTEST heating pad has an electronic control connected by a wire to the pad which provides four temperatures settings and automatic shutoff after 30 minutes. The heating pad has a cloth cover with a strap to secure the pad in place and a moistening sponge pad. KA SMARTEST is a trademark for a heating pad obtainable from Comfort House, Newark, N.J.

The prior art does not disclose the heater or cooler of this invention in which a flexible conformal container loaded with thermally conductive material is heated by a PTC heater or cooled by a thermoelectric device mounted on the outside of the container. The heater or thermoelectric device is powered by low voltage direct current which is controlled by a controller in response to the temperature of the thermally conductive material in the container as sensed by a thermoelectric device sensor.

BRIEF SUMMARY OF THE INVENTION

This invention is a flexible heater or cooler which includes a flexible, conformal, thermally conductive container filled with thermally conductive material. A thermal element within the container or in contact with the outside of the container provides heat to the container or removes heat from the container. The thermal element is powered by a low voltage direct current electrical source. A sensor for determining the temperature of the thermally conductive material is also included. The thermal element, electrical source, and sensor are in communication by connectors with a solid state continuous temperature controller. In operation, the electrical source provides power to the thermal element, thereby heating or cooling the thermally conductive material within the container. The temperature in the container is determined by the sensor and the controller controls the power delivery to the thermal element in response to the setting on the controller and the temperature in the container.

The objective of this invention is to provide a flexible, conformal heater or cooler for application to sore or distressed areas of the body.

Another objective is to provide a heater for regulated industrial heating or cooling applications.

Another objective is to provide a heater with provisions to prevent overheating.

Another objective is to provide a heater or cooler which is powered by low voltage direct current electricity.

Another objective is to provide a heater or cooler which does not emit ENF radiation.

Another objective is to provide a heater which inherently limits the maximum temperature attainable.

Another objective is to provide a heater which avoids the hazards of accidental electrical shock.

Another objective is to provide a heater or cooler with user control of the temperature.

A final objective is to provide a flexible conformal heater or cooler which is constructed easily and inexpensively of common materials and whose manufacture and use is without adverse effects on the environment.

DETAILED DESCRIPTION OF THE INVENTION

The invention has several components, a container which contains thermally conductive material, a heating or cooling element located within the container or attached to the outside, a temperature sensor located inside the container, and a controller and power source.

Figure 1:
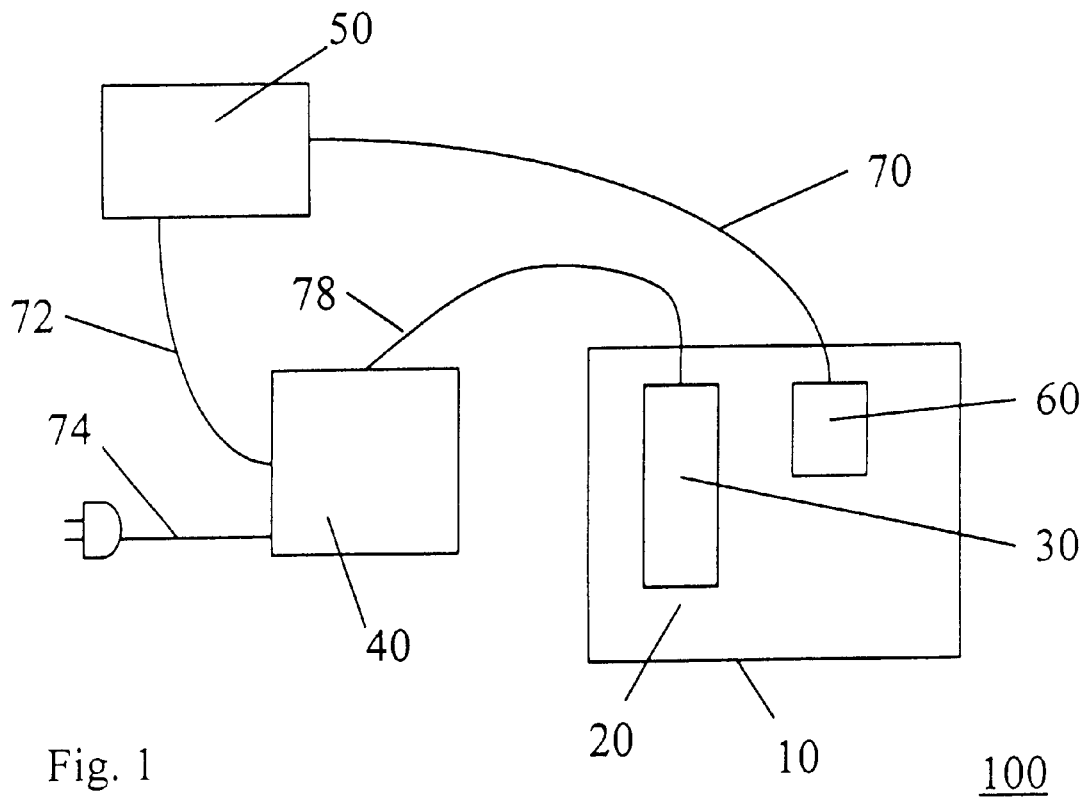
FIG. 1 is a schematic diagram of a first embodiment heater with an internal resistance heater element.

FIG. 1 is a diagrammatic representation of the first embodiment heater 100. The container or bag 10 holds the thermally and electrically conducting gel 20. A thermocouple safety sensor 60 is immersed in the gel 20. A resistance heater 30 is also immersed in gel 20. A controller 50 controls the operation of the heater. Power supply 40 converts AC line voltage to 12 volt DC current to power the heater 30 and sensor 60. The sensor is connected to the controller by connector 70. The controller is connected to the power supply by connector 72. The power supply is connected to the resistance heater 30 by connector 78. The power supply 40 is connected to the line voltage supply by connector 74. The controller 50 and power supply 40 may be combined in a single housing.

Figure 2:
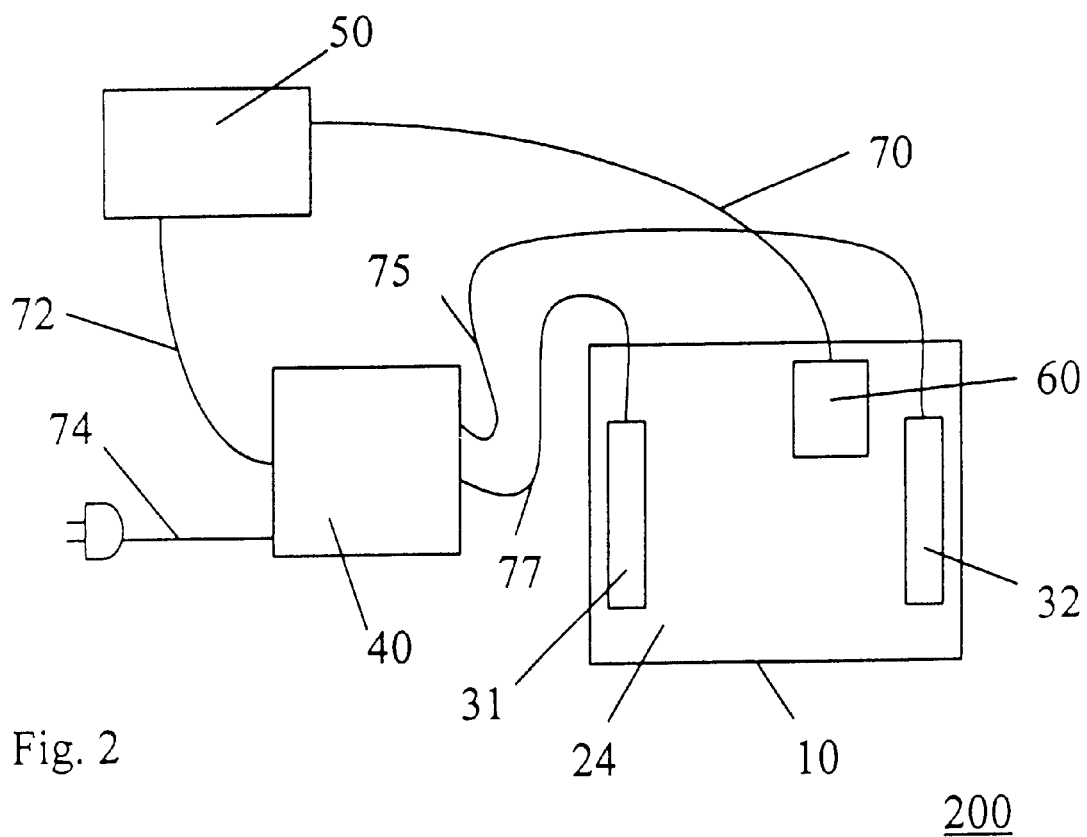
FIG. 2 is a schematic diagram of a second embodiment heater with a PTC heater element.

FIG. 2 is a diagrammatic representation of the second embodiment heater 200. The second embodiment heater is identical to the first embodiment heater 100 shown in FIG. 1 except there is no resistance heater 30. The heat is provided by a PTC heater which comprises thermally and electrically conducting gel 24 into which are immersed two strip-like electrodes 31 and 32. Electrical current at 12 volt DC is passed through the gel 24 between the electrodes 31 and 32, thereby heating the gel 24. Electrode 31 is connected by connector 77 to power supply 40. Electrode 32 is connected by connector 75 to power supply 40.

Figure 3:
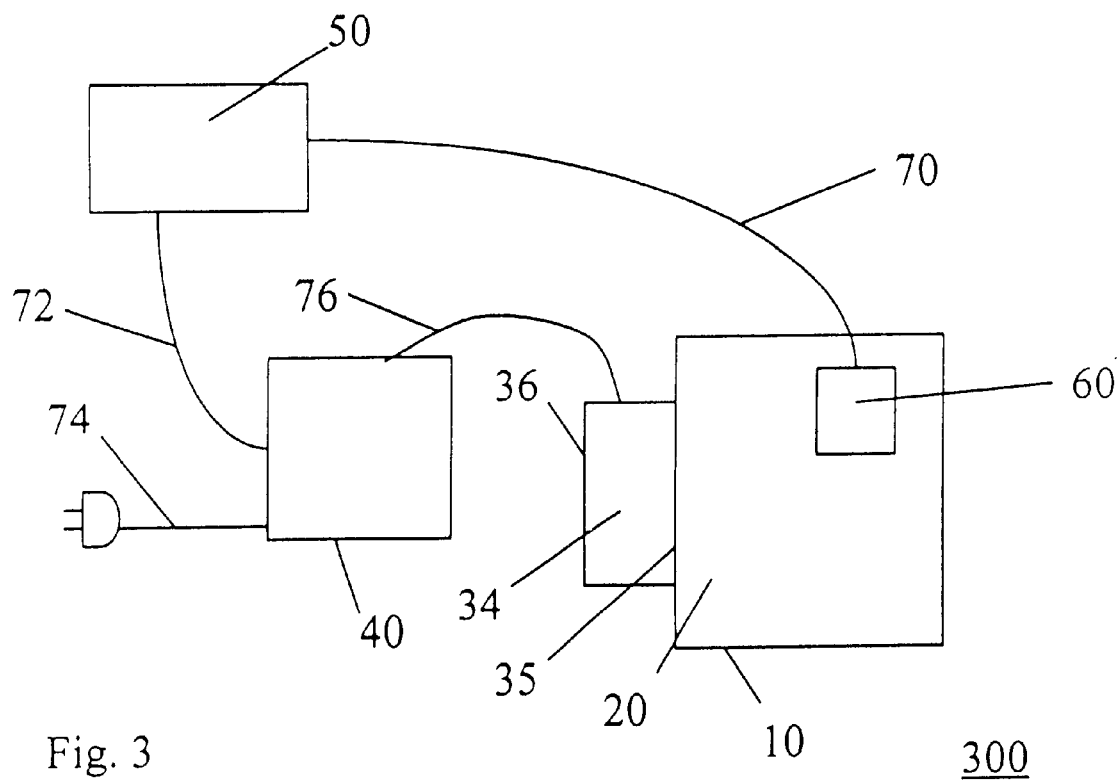
FIG. 3 is a schematic diagram of a first embodiment heater and cooler with an external heater and cooler element.

FIG. 3 is a diagrammatic representation of the first embodiment heater and cooler 300. The second embodiment heater and cooler is identical to the first embodiment heater 100 shown in FIG. 1 except there is no resistance heater 30. A thermoelectric cooling and heating unit 34 based on the Peltier effect is mounted on the outside of the container 10. The cooling and heating unit 34 is connected to the power supply 40 by connector 76. The unit 34 has side 35 in thermal contact with the container 10 and a side 35 in thermal contact with ambient air. In operation as a cooler side 35 is cooled and cools the container 10. Side 36 is heated and the heat is dissipated into the air. When the polarity of current to the thermoelectric cooling and heating unit 34 is reversed, side 35 becomes heated, as does container 10, and side 36 becomes cooled.

Figure 4:
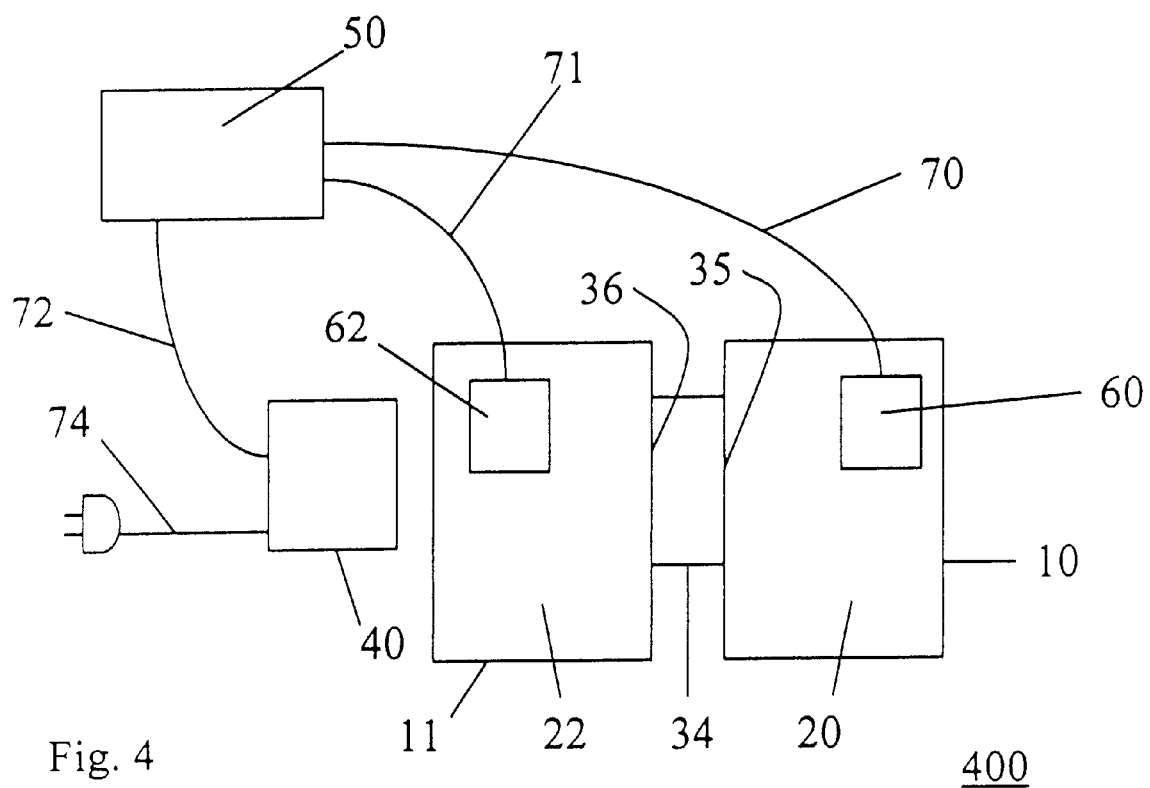
FIG. 4 is a schematic diagram of a second embodiment heater and cool with an external heater and cooler element attached to two containers.

FIG. 4 is a diagrammatic representation of the second embodiment heater and cooler 400. The second embodiment heater and cooler is identical to the first embodiment heater and cooler 300 shown in FIG. 3 except that a second container 11 containing thermally and electrically conducting gel 22 and a sensor 62 is in thermal contact with the thermoelectric cooling and heating unit 34 on the side 36. In operation, if container 10 is cooled, container 11 is heated. Reversal of the polarity to unit 34 causes container 10 to be heated and container 11 to be cooled. This is particularly useful for alternative heating and cooling of affected body parts.

Further details on the component elements of the first and second embodiment heaters and first and second embodiment cooler and heaters are described below.

Container

Any strong, impervious to fluids, conformable, flexible container or bag may be used to contain the gel. If the bag is multilayered, the inner layer should be heat sealable. Suitable bags are disclosed in U.S. Pat. No. RE34,929, incorporated herein by reference. The layers of a multilayered bag can be made of different materials, for example, the inner layer may be of polyethylene or polypropylene, or polyvinyl chloride, and the outer layer of polyester or nylon or MYLAR brand of polyester film, obtainable from Dupont, Wilmington, Del. Additional layers may be present, for example, an intermediate layer of high density polyethylene, or closed cell polyethylene foam. A preferred 3-ply VACLOCK brand multilayer bag is obtained from Tilia, Inc., San Francisco, Calif. It is not necessary that the container be constructed of gas impermeable material, although the container must be impervious to fluids. Polystyrene; as well as MYLAR brand of polyester film, obtainable from DuPont, Wilmington, Del.; KAPTON brand of polyimide film, obtainable from Circleville, Ohio; SARAN brand of thermoplastic film obtainable from Johnson and Sons, Inc., Racine, Wis.; or silicone films may be used. Each layer in a bag is about 0.5 to 3.0 mil thick. Metal foils, such al aluminum foil, may be included in a multilayer container.

FIGS. 5A–5F are diagrammatic representations of the cross-sections of preferred containers.

Figure 5A:
FIG. 5A is a cross section of a two layer container.

FIG. 5A shows a two-layer container comprised of MYLAR film 11 and polyethylene 12 1m.

Figure 5B:
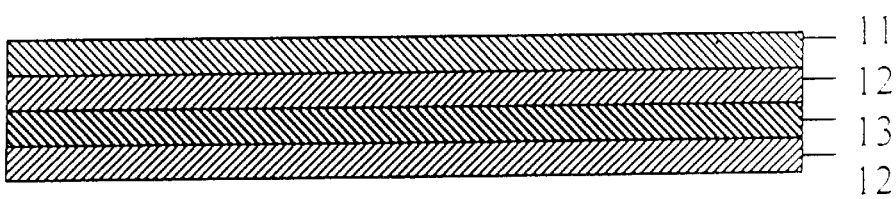
FIG. 5B is a cross section of a four layer container.

FIG. 5B shows a four-layer container comprised of MYLAR film 11 attached to polyethylene film 12, which is in turn attached to one side of aluminum foil 12. A polyethylene film 12 is attached to the other side of the aluminum foil 12.

Figure 5C:
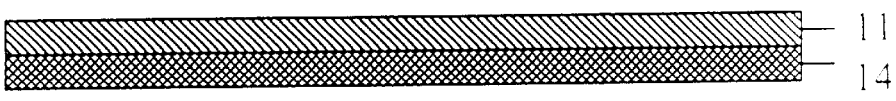
FIG. 5C is a cross section of a two layer container.

FIG. 5C shows a two-layer container comprised of MYLAR film 11 attached to closed cell polyethylene foam 14.

Figure 5D:
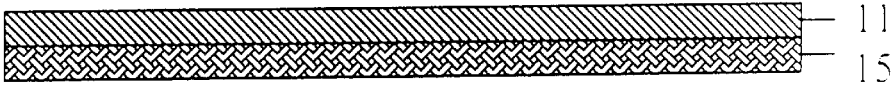
FIG. 5D is a cross section of a two layer container.

FIG. 5D shows a two-layer container comprised of M AR film 11 attached to SARAN film.

Figure 5E:
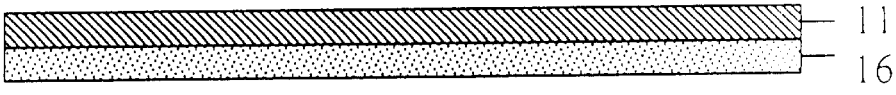
FIG. 5E is a cross section of a two layer container.

FIG. 5E shows a two-layer container comprised of MYLAR film 11 coated with an adhesive film 16.

Figure 5F:
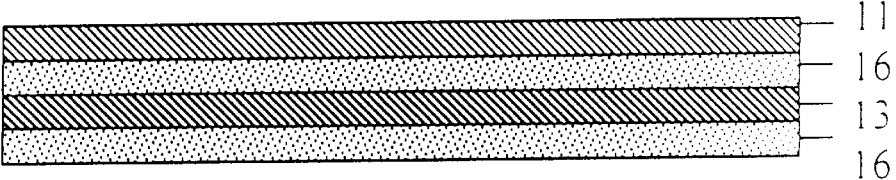
FIG. 5F is a cross section of a four layer container.

FIG. 5F shows a four-layer container comprised of MYLAR film 11 attached on one side to adhesive film 16, which is in turn attached to aluminum foil 13, and the aluminum foil 13 is coated with an adhesive film 16.

PTC Heating

Heating is achieved by the passage of 12 volt direct current electrical current between two electrodes immersed in the thermally and electrically conductive material referred to as "PTC" materials. PTC is an acronym for positive temperature coefficient of resistance. Such PTC materials have the desirable property increasing electrical resistance with increase in temperature, and therefore automatically limit the temperature achieved by the heater. This provides an additional safety factor for the user of the pad in the heating mode. The electrodes may be parallel columns of wires immersed in the thermally and electrically conductive material or laminal electrodes in the shape of metal foil or mesh. Any suitable highly electrically conductive material may be used for the electrodes, such as copper, nickel, aluminum, or silver. A preferred material is nickel or copper.

Thermally and Electrically Conductive Material

The container is filled with a thermally and electrically conducting material which preferably is a thermally conductive gel. The containers are flexible and conform to the portion of the body which is being heated. A gel is constituted of two components, a liquid phase, and a solid phase.

The liquid phase may be water based, or based on non-aqueous liquid polymers, such a silicone oil, mineral oil or another petrochemical-origin oil, polyvinylidene fluoride, and a crystalline copolymer consisting essentially of units derived from at least one olefin and at least 10% by weight, based on the copolymer, of units derived from at least one olefinically unsaturated comonomer containing a polar group. The solid phase or particulate conductive filler of the gel is particles of silica, alumina, titania, iron oxide, zinc oxide, aluminum oxide, carbon black, graphite, or ceramics. When non-aqueous liquid phase is used, ionic salts such as sodium chloride, magnesium sulfate, copper sulfate may be used as the solid phase.

The composition of the thermally and electrically conductive material determines the resistivity and therefore the heating characteristics of the heating pad. Higher resistivity material results in higher temperature generation by the heater. Resistivity is increased by lowering the proportion of conductive filler in the gel; resistivity is decreased by increasing the proportion of conductive filler in the gel. A suitable formulation comprises 10%–90% by weight petroleum jelly as the sol phase and 10%–90% by weight zinc oxide particles as the solid phase. A preferred formulation comprises 25% by weight petroleum jelly and 75% by weight zinc oxide particles.

Resistance Heating

In a second embodiment heater, resistance wire heaters are used to provide the heat to thermally conductive material. In this embodiment, gel is used as the thermally conductive material, although it is not necessary that the material be electrically conductive. The resistance heater elements are made of any suitable resistance heating material, a preferred material is Nichrome. Resistance wire elements are immersed in the thermally conductive material, and may be straight or coiled in form. Preferably the resistance elements are laminated between layers of flexible films, such as between layers of MYLAR, KAPTON, or silicon film. A preferred resistance wire tape is an insulated tape suitable for use in an electrically conductive environment, such as Dw-Tape, AWH, manufactured by Amptek Company, Stafford, Tex. Another preferred heater is Model PR 735A07053003 manufactured by American Thermal Products, St. Marys, Pa.

Cooling Element

The heating and cooling pad is cooled using a thermoelectric cooling unit based on the Peltier Effect mounted on the outside of the container. Such a cooler is based on the cooling at one junction of a thermoelectric device circuit associated by the passage of a current through the circuit. The cooler has no moving parts. It is mounted on the outside of the container to permit heat produced at the other junction of the thermoelectric device circuit to be dissipated into the air. An electric fan aids in removing the heat from the cooling element. Reversal of the polarity of the electricity supplied to the thermoelectric cooling unit reverses the effect from cooling to heating the container. This may be used when alternative heating and cooling of affected body parts is desired.

In another embodiment, the thermoelectric cooling agent is mounted between two containers.

One container is heated while the other one is cooled.

A suitable cooling element is the SCTB NORD 300 watt unit obtainable from Advanced Thermoelectric Products, Nashua, N.H.

Sensor

A thermoelectric device or thermistor safety sensor is immersed in the conductive material of the heater and cooler. This sensor turns off the heater if the temperature in the container exceeds a preset level. In addition, the heater is turned off if the sensor fails. A suitable sensor is a type T thermoelectric device with copper and constantan junctions which has a range of measurement of −330 to 660° F. Such sensors can be obtained from Instrument Service & Equipment, Inc., Cleveland, Ohio.

Controller

The controller controls flow of 12 volt DC current to the heater or cooler elements in response to signals from the thermoelectric device sensor which indicate the temperature inside the container. In addition, the controller has an on/off switch and a continually variable temperature setting dial (not shown in the Figs.).

Figure 6:
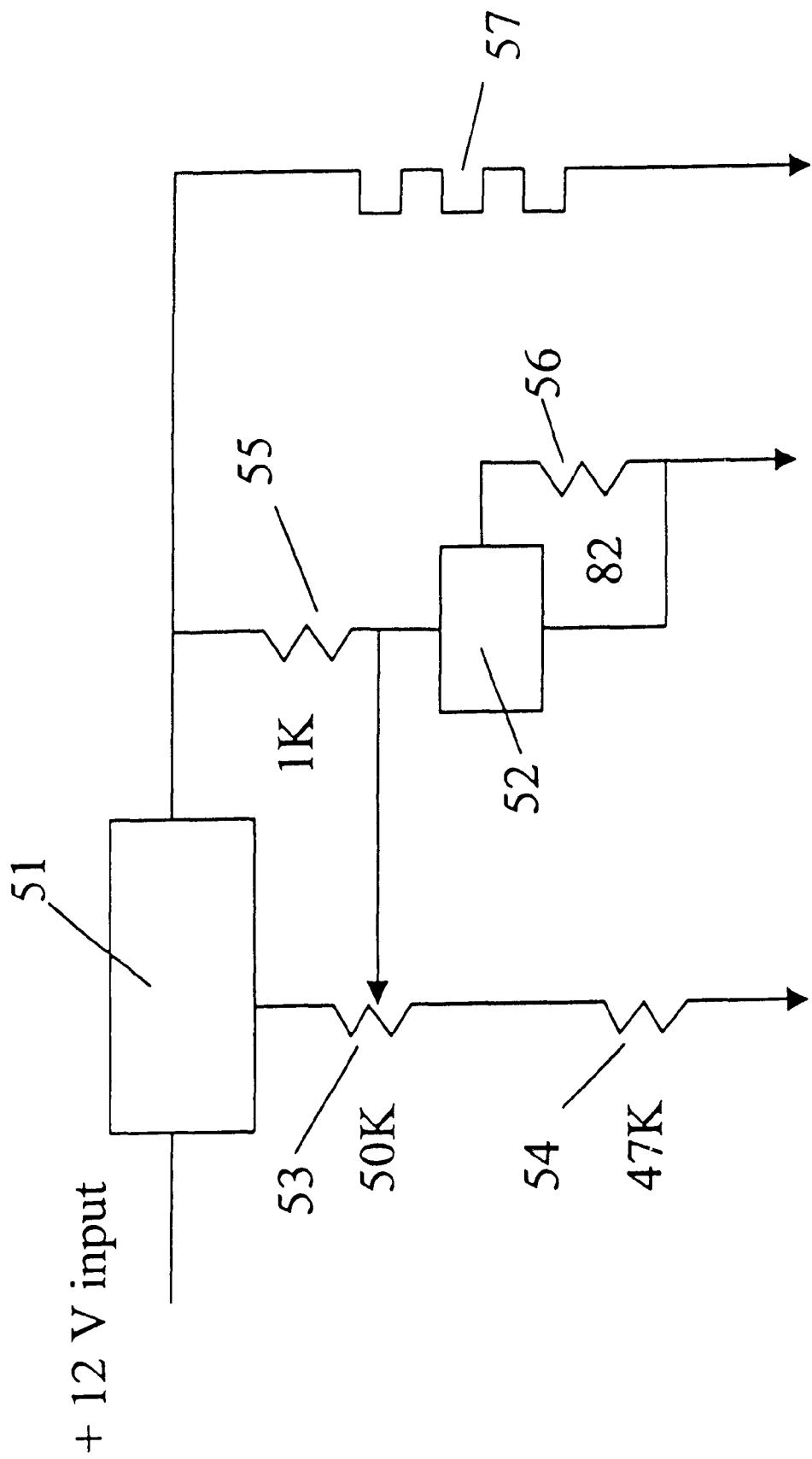
FIG. 6 is a schematic diagram of the controller.

FIG. 6 is a schematic diagram of the controller elements. A current source 51 and regulator 50 are shown, along with resistors 53, 54, 55, and 56 with indicated resistances, and resistance heater 57. A preferred current source is a 3-terminal adjustable current source Model LM 334, manufactured by National Semiconductor Corporation, Santa Clara, Calif. It has a 10,000 to 1 range. in operation current and a voltage range of 1V to 40V. A preferred regulator is a 5-amp adjustable regulator, a 3-terminal positive voltage regulator capable of supplying over 5A over a 1.2V to 32 V output range, Model LM 338, manufactured by National Semiconductor Corporation, Santa Clara, Calif. A preferred resistance heater is Model PR 735A0705300B, manufactured by Advanced Thermal Products, St. Marys, Pa.

It will be apparent to those skilled in the art that the examples given here are illustrative only, and that this invention is limited only by the appended claims.

We claim:

1. A flexible heater comprising in combination:

a flexible, conformal, thermally conductive container filled with thermally conductive gel, a thermoelectric element for heating the container, the thermoelectric element in contact with the outside of one or more flexible conformal containers filled with thermally conductive gel and heats the one or more flexible conformal containers filled with thermally conductive gel, wherein the thermally conductive gel does not change phase during the operation of the flexible heater and comprises a polymeric component and a particulate filler, a low voltage direct current electrical source, a sensor for determining the temperature of the thermally conductive gel, a solid state continuous temperature controller, and connectors for connecting the thermal element, solid state continuous temperature controller, sensor, and low voltage direct current electrical source.

2. A flexible cooler comprising in combination:

a flexible, conformal, thermally conductive container filled with thermally conductive gel, a thermoelectric element for cooling the container, the thermoelectric element in contact with the outside of one or more flexible conformal containers filled with thermally conductive gel and cools the one or more flexible conformal containers filled with thermally conductive gel, wherein the thermally conductive gel does not change phase during the operation of the flexible cooler and comprises a polymeric component and a particulate filler, a low voltage direct current electrical source, a sensor for determining the temperature of the thermally conductive gel, a solid state continuous temperature controller, and connectors for connecting the thermal element, solid state continuous temperature controller, sensor, and low voltage direct current electrical source.

* * * * *